Figure 3:
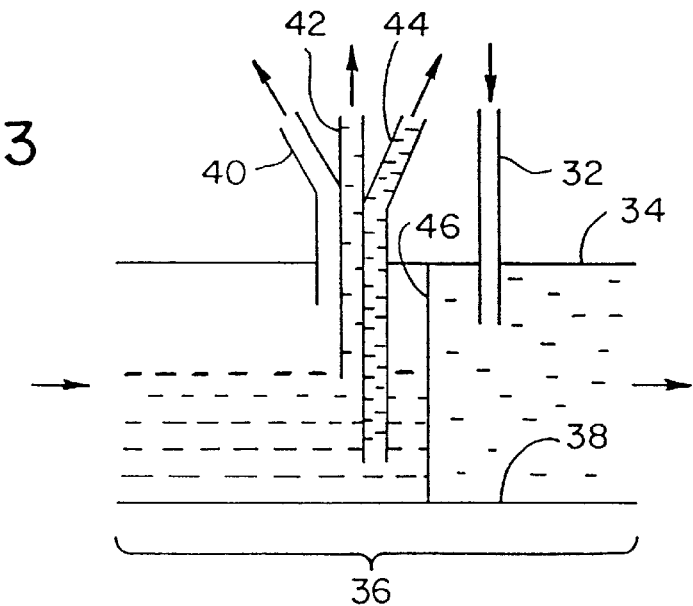

United States Patent [19]
Borchardt et al.

[11] Patent Number: 5,961,846
[45] Date of Patent: *Oct. 5, 1999

[54] CONCENTRATION OF WATERBORN AND FOODBORN MICROORGANISMS

[75] Inventors: Mark A. Borchardt, Marshfield; Susan K. Spencer, Spencer, both of Wis.

[73] Assignee: Marshfield Medical Research and Education Foundation, Marshfield, Wis.

[*] Notice: This patent is subject to a terminal disclaimer.

[21] Appl. No.: 09/017,832

[22] Filed: Feb. 3, 1998

Related U.S. Application Data

[63] Continuation-in-part of application No. 08/969,462, Aug. 11, 1997, Pat. No. 5,858,251, which is a continuation-in-part of application No. 08/608,422, Feb. 28, 1996, Pat. No. 5,846,439.

[51] Int. Cl.⁶ .................................................. B01D 21/26
[52] U.S. Cl. ......................... 210/781; 210/787; 422/72; 422/101; 494/37; 494/43
[58] Field of Search ................................. 210/781, 787, 210/360, 380.1; 422/72, 101; 494/41, 43, 70, 37

[56] References Cited

U.S. PATENT DOCUMENTS

| | | |
|---|---|---|
| 3,217,982 | 11/1965 | Wilsmann et al. . |
| 4,010,894 | 3/1977 | Kellogg et al. . |
| 4,094,461 | 6/1978 | Kellogg et al. . |
| 4,386,730 | 6/1983 | Mulzet . |
| 4,387,848 | 6/1983 | Kellogg et al. . |
| 4,419,089 | 12/1983 | Kolobow et al. . |
| 4,430,072 | 2/1984 | Kellogg et al. . |
| 4,439,178 | 3/1984 | Mulzet . |
| 4,447,221 | 5/1984 | Mulzet . |
| 4,647,279 | 3/1987 | Mulzet et al. . |
| 4,708,712 | 11/1987 | Mulzet . |
| 4,850,995 | 7/1989 | Tie et al. . |
| 4,900,298 | 2/1990 | Langley . |
| 5,100,372 | 3/1992 | Headley ................................... 494/41 |
| 5,217,427 | 6/1993 | Cullis . |
| 5,356,365 | 10/1994 | Brierton . |
| 5,571,068 | 11/1996 | Bacehowkski et al. . |

OTHER PUBLICATIONS

Whitmore et al., *Wat. Sci. Tech.* 27 (3–4):69–76.

Clancy et al. *Journal of the American Water Works Association* (1994), 86:89–97.

Goatcher et al., *American Society of Macrobiology Abstracts* (1995), Q–212.

(List continued on next page.)

*Primary Examiner*—David A. Reifsnyder
*Attorney, Agent, or Firm*—DeWitt Ross & Stevens SC

[57] ABSTRACT

A method of concentrating microorganisms, particularly pathogenic microorganisms, from food and/or water potentially contaminated by dilute densities of the organisms is described. Potentially contaminated water or fluid food is directed along an elongated flow path which rests generally within a plane perpendicular to an axis of rotation, and is subjected to centrifugal forces by rotating the flow path about the rotational axis. The method may be executed by use of a conventional continuous flow channel-type blood plasmapheresis centrifuge.

43 Claims, 5 Drawing Sheets

OTHER PUBLICATIONS

Addiss et al., Assessing the Public Health Threat Associated with Waterborne Cryptosporidiosis: Report of a Workshop, *Morbidity and Mortality Weekly Report* (Jun. 16, 1995), 44 (RR–6):1–19.

Colford et al., Cryptosporidiosis among Patients Infected with Human Immunodeficiency Virus, *American Journal of Epidemiology* (1996), 144(9):807–816.

*Cryptosporidium Capsule* (Apr. 1996), vol. 1, Issue 6.

Ditrich et al., The first finding of *Crytosporidium baileyi* in man, *Parasitol Res.* (1991), 77:44–47.

Goldstein et al., Cryptosporidiosis: An Outbreak Associated with Drinking Water Despite State–of–the–Art Water Treatment, Annals of Internal Medicine (Mar. 1, 1996) 124(5):459–468.

Guarino et al., Enteric Cryptosporidiosis in Pediatric HIV Infection, *Journal of Pediatric Gastroenterology and Nutrition* (1997), 25:182–187.

Hoxie et al., Cryptosporidiosis–Associated Mortality Following a Massive Waterborne Outbreak in Milwaukee, Wisconsin, *American Journal of Public Health* (Dec. 1997), 87(12):2032–2035.

Juranek et al., Cryptosporidiosis: Sources of Infection and Guidelines for Prevention, *Clinical Infectious Diseases* (1995), 21 (Suppl 1): S57–61.

Pozio et al., Clinical Cryptospordiosis and Human Immunodeficiency Virous (HIV)–Induced Immunosuppression: Findings from a Longitudinal Study of HIV–Positive and HIV–Negative Former Injection Drug Users, *The Journal of Infectious Diseases* (1997), 176:969–75.

Selik et al., Effect of the Human Immunodeficiency Virus Epidemic on Mortality from Opportunistic Infections in the United States in 1993, *The Journal of Infectious Diseases* (1997), 176:632–636.

Ad for drug/dietary supplement from *Crytpo Immune* (Feb. 1, 1998).

Excerpt from *Helix Water Districts's 1996 Water Quality Reports* (Feb. 1, 1998).

FIG. 1
PRIOR ART
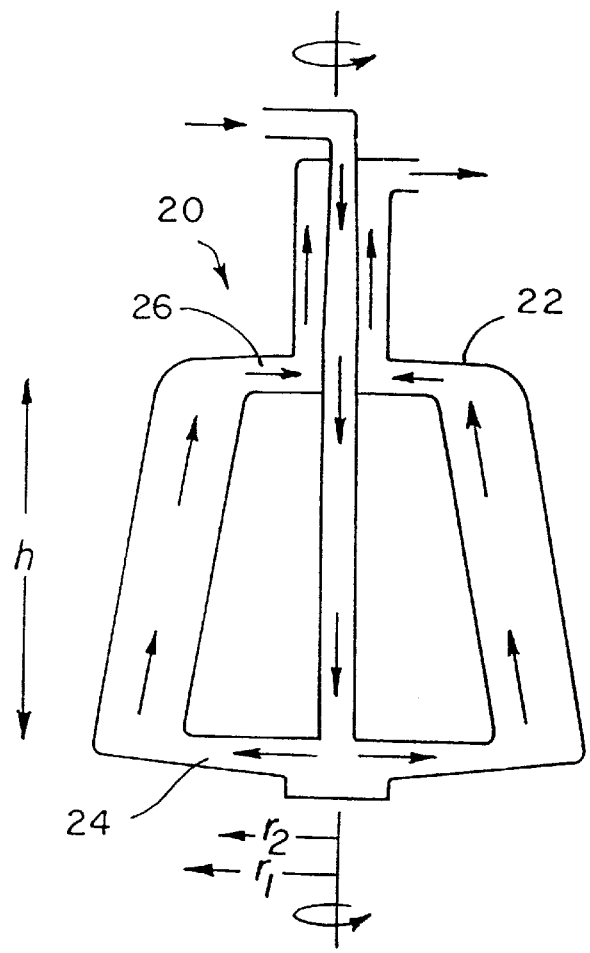
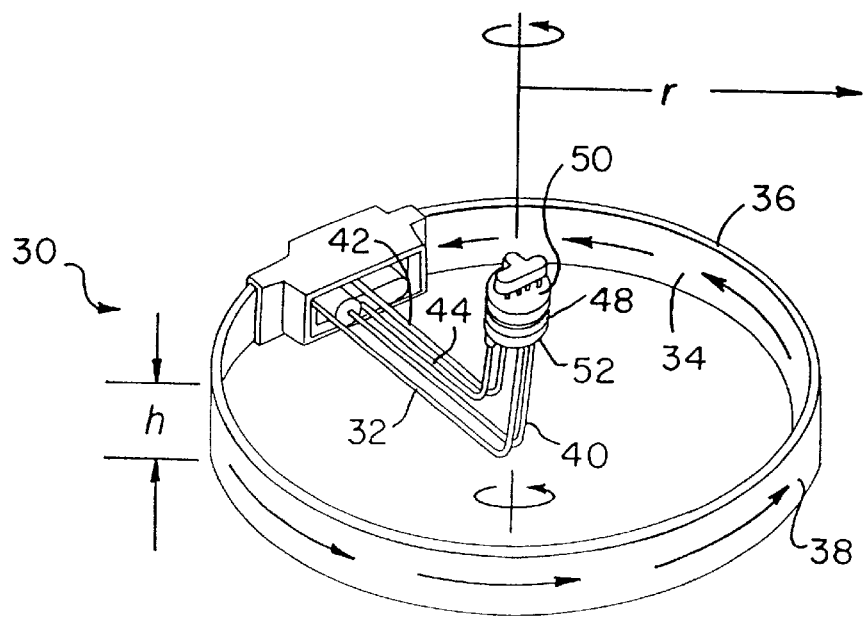
FIG. 2

CONCENTRATION OF WATERBORN AND FOODBORN MICROORGANISMS

CROSS-REFERENCE TO RELATED APPLICATIONS

This application is a continuation-in-part of U.S. patent application Ser. No. 08/969,462 filed Aug. 11, 1997, entitled Concentration of Waterborne Pathogenic Organisms, now U.S. Pat. No. 5,858,251, which is a continuation-in-part of U.S. patent application Ser. No. 08/608,422 filed Feb. 28, 1996, entitled Method of Concentrating Waterborne Protozoan Parasites, now U.S. Pat. No. 5,846,439 both of which are incorporated by reference herein.

FIELD OF THE INVENTION

The present invention is directed to a method of concentrating waterborne and foodborne microorganisms from fluids potentially contaminated by such microorganisms.

BACKGROUND OF THE INVENTION

Despite advances in water and food processing, outbreaks of disease from waterborne and foodborne pathogens still occur frequently in the United States. Bacterial water- and foodborne pathogens include Clostridium species, e.g., *Clostridium botulinum* (botulism) and *Clostridium perfringens* (food poisoning); *Staphylococcus aureus* and other staphylococci (food poisoning); Streptococcus species (gastroenteritis); enteropathogenic strains of *Escherichia coli* (gastroenteritis); Shigella species, e.g., *Shigella dysenteriae* (dysentery), and *Shigella flexneri* and *Shigella sonnei* (gastroenteritis); *Bacillus cereus* (gastroenteritis); Salmonella species, e.g., *Salmonella enteritidis* and *Salmonella paratyphi* (gastroenteritis), as well as *Salmonella typhi* (typhoid fever); the Salmonella-like *Arizona hinshawii; Yersinia enterocolitica* (gastroenteritis); *Vibrio parahemolyticus* (gastroenteritis); *Vibrio cholerae* (cholera); species of Campylobacter (gastroenteritis); species of Leptospira (leptospirosis); Brucella species (undulant fever); *Francisella tularensis* (tularemia); and *Listeria monocytogenes* (listeriosis). There are also numerous water- and foodborne protozoan pathogens, such as *Entamoeba histolytica, Giardia lamblia,* Cryptosporidium, Microsporidia, and Cyclospora. Many of these organisms can infect humans via either foodborne or waterborne routes (e.g., Salmonella), while others are more particularly limited to transmission through either water or food.

In an attempt to avoid disease, food and water is often sampled and tested prior to distribution to determine whether the food/water is contaminated by pathogenic organisms. Numerous testing methods are available, but the following steps (or similar steps) are common to many methods (particularly those involving bacteria rather than protozoan organisms):

First, a pre-enrichment step is performed on the sample to increase the number of pathogenic organisms present. The organisms are cultured in a non-selective growth medium, e.g., trypticase soy broth or peptone water, typically for 24 hours or more. The pre-enrichment step is disadvantageous because it is generally inconvenient to stall distribution of water or fresh foodstuffs while their samples are culturing, particularly where freshness or spoilage concerns are present or the food/water is unwieldy to store. However, pre-enrichment is usually necessary because pathogenic organisms may be present in very dilute amounts, thus making them difficult to detect.

Second, an enrichment step is performed wherein a portion of the culture medium is transferred to an enrichment medium containing inhibitors that select for a pathogen of interest. The selected pathogen will grow further while other organisms are inhibited. This step, which essentially furthers the concentration of pathogens begun by the pre-enrichment step, can also be inconvenient and time-consuming.

Third, a measurement step is performed to discern whether pathogens of interest are present. Generally, a portion of the enrichment medium is streaked onto selective/differential agar media. The media will contain inhibitors effective against most organisms except the pathogen of interest. Indicator compounds (e.g. dyes) allow pathogen types to be differentiated, and thus indicate the presence and number of pathogens of interest. Exemplary alternative measurement steps are radioimmunoassay (RIA) tests, immunofluorescent assay (IFA) tests, enzyme immunoassay (EIA) tests, DNA methods (e.g., PCR), and phage methods. IFA and DNA methods are generally used to detect protozoan pathogens in lieu of the other methods noted above.

If pathogenic organisms are detected in the food/water, the food/water can be destroyed or withdrawn prior to consumption. Alternatively, it can be treated to eliminate or substantially reduce the presence of pathogens. Filtration, pasteurization, chemical treatment (e.g., chlorination or ozonation), and radiation treatment are common methods of reducing or eliminating pathogens from food/water.

U.S. Pat. No. 3,217,982 to Wilsmann et al. illustrates a method of reducing pathogens (specifically bacterial pathogens) within beverages by use of continuous flow bowl centrifugation. As an introduction to continuous flow bowl centrifugation, an exemplary continuous flow bowl centrifuge (commonly referred to as a Latham bowl centrifuge) is shown at 20 in FIG. 1. Fluid is introduced into the end (top or bottom) of a spinning bowl 22 from an axially-directed input line 24 with length r1 located near the rotational axis of the bowl 22. As the fluid flows up the height h of the bowl 22, centrifugal force forms a density gradient in the fluid with the densest (heaviest) matter (e.g., food particles or other detritus) located near the wall of the bowl 22 and the lighter matter (e.g., water) being located closer to the rotational axis. As liquid is introduced into the bowl 22, the lighter portion of the fluid is emptied at the same flow rate from an axially-situated and axially-directed exit line 26 with length r2 which exits the end of the bowl 22 opposite the input line 24. The Wilsmann et al. invention utilizes continuous flow bowl centrifugation to remove microorganisms from beverages by heating the beverage during centrifugation, and also by providing dual exit lines, one of which is used to draw off the heavy microorganism-rich fraction for removal from the beverage and the other being used to draw off the lighter microorganism-depleted fraction for later consumption.

However, studies of continuous flow bowl centrifugation wherein contaminated fluid is centrifuged without heating have found that continuous flow bowl-type centrifugation alone is not efficient in concentrating pathogens from the water/food. Some studies of bowl-type continuous flow centrifuge for concentration of Cryptosporidium oocysts report recovery efficiency to be between 11% to 31.2%. Whitmore et al., *Wat. Sci. Tech.* 27 (3–4): 69–76, 1993. Goatcher et al. also tested a bowl-type continuous flow centrifuge system in the concentration of Cryptosporidium oocysts from water and reported obtaining recovery rates of between 2 to 20 times those observed with an ASTM filtration method. *American Society of Microbiology Abstracts* Q-212, 1995. Since Clancy et al. report that the ASTM method provides Cryptosporidium recovery rates averaging around 2.8%, such recovery rates are still well under 50%. *Journal of the American Water Works Association* 86: 89–97, 1994.

When it is then considered that protozoan Cryptosporidium oocysts are among the largest food/waterborne pathogens and thus should achieve a higher degree of concentration during centrifugation than smaller bacterial pathogens (in accordance with Stokes' equation), it can be expected that even lower recoveries of bacterial pathogens would result from centrifugation. As a result, even though continuous flow centrifugation is generally cheaper and less time-consuming than filtration, it has not gained acceptance as a method for concentrating pathogens from fluids and providing accurate measures of their total count therein. Owing to the importance of detecting waterborne and foodborne pathogens and preventing their transmission to the general population, it would clearly be beneficial to have an inexpensive, rapidly-performed, and accurate method available for the concentration of such pathogens.

SUMMARY OF THE INVENTION

The present invention, which is defined by the claims set out at the end of this disclosure, is directed to the concentration of microorganisms from food and water. One aspect of the invention concerns a method of concentrating microorganisms from food or water potentially contaminated by dilute densities of the organisms wherein the water or fluidized food is fed into an elongated flow path, e.g., a flow path defined by a channel or duct. The flow path includes a separation section wherein the food/water flow is oriented in directions substantially tangential with respect to a rotational axis. The flow path is then subjected to centrifugal forces by spinning it about the rotational axis in such a manner that the centrifugal forces are oriented substantially perpendicular to the separation section. This highly concentrates microorganisms within the food/water flowing within the separation section, and can decrease or eliminate the time and burden of performing pre-enrichment and enrichment culturing steps. Since all organisms within the separation section are concentrated, the need to prepare and enrich separate samples for separate microorganisms can also be reduced or eliminated.

Examples of apparata for performing this method are channel-type blood centrifuges, e.g., the IBM (COBE) model 2997 channel-type blood centrifuge (formerly made by International Business Machines, Armonk, N.Y. USA and now made by COBE, Lakewood, Colo., USA) or the COBE Spectra channel-type blood centrifuge. Such channel centrifuges, which are discussed at greater length later in this disclosure, utilize hollow hoop-shaped separation channels with the rotational axis being situated at the center of the hoop. Radially-directed input and exit lines are connected to the separation channel in much the same manner as spokes leading to a wheel. Fluid supplied to the centrifuge travels radially outward in the input line, enters the separation channel and traverses its circumference, and then travels radially inward through the exit line. When the separation channel is spun about the rotational axis, centrifugal forces oriented perpendicular to the channel are generated.

Another aspect of the invention concerns a method of concentrating microorganisms from food or water by feeding the water or fluidized food into an elongated flow path. The flow path includes a separation section wherein the food/water flow follows an arcuate path defined about a rotational axis. Microorganisms within the food/water in the separation section are then concentrated by spinning the flow path about the rotational axis, thereby creating centrifugal forces substantially perpendicular to the separation section. This aspect of the invention may be practiced by utilizing the channel centrifuges noted above, wherein the hoop-like channel serves as the separation section. Alternatively, it may be practiced by use of channels in the shape of ellipses, helixes, parabolic sections, or channels of other shapes which orbit or curve about the rotational axis.

A further aspect of the invention involves a method of concentrating microorganisms from food or water by feeding the water or fluidized food into a flow path which includes a separation section resting within a plane (or planes) oriented generally perpendicular to the rotational axis. The separation section has a length greater than 2 r, where r is the average of the maximum and minimum radial distances of the flow path from the rotational axis. Microorganisms within the food/water in the separation section are then concentrated by spinning the flow path (including the separation section) about the rotational axis, thereby subjecting it to centrifugal force. The aforementioned hoop-like channel centrifuge provides an example of a preexisting device which may be used to practice this embodiment of the method.

The various aspects of the invention summarized above are believed to have less process and apparatus/material costs, less time and labor requirements, and higher effectiveness than any previously known methods and apparata for concentrating pathogenic microorganisms in food or water. Other advantages and features of the invention will be apparent from the remainder of this disclosure.

BRIEF DESCRIPTION OF THE DRAWINGS

FIG. 1 is a schematic cross-sectional view of a prior art continuous flow bowl centrifuge.

FIG. 2 is a perspective view of the channel assembly of a continuous flow channel centrifuge.

FIG. 3 is a schematic diagram of a section of the channel of FIG. 2 illustrating the channel input and outlet lines in greater detail.

FIG. 4 is a perspective view of another embodiment of a channel assembly encompassed by the invention.

FIG. 5 is a schematic diagram of a section of the channel of FIG. 4 illustrating the channel input and outlet lines in greater detail.

FIG. 6 is a schematic diagram of a section of an alternate embodiment of a channel illustrating the channel input and outlet lines in greater detail.

FIGS. 7–11 are perspective views of alternate embodiments of channel assemblies encompassed by the invention.

FIG. 12 is a schematic diagram of a section of an alternate embodiment of a channel illustrating the channel input and outlet lines in greater detail.

DETAILED DESCRIPTION OF THE INVENTION

Continuous Flow Channel-Type Centrifuges

A separation channel assembly from a typical channel-type continuous flow centrifuge, which may be used to concentrate pathogenic organisms in accordance with the present invention, is depicted in FIG. 2 at reference numeral 30. The channel assembly 30 depicted in FIG. 2 is part of an IBM model 2997 blood separation channel centrifuge. The division of IBM which manufactured the channel assembly 30 pictured in FIG. 2 is now owned by COBE Corporation, Lakewood, Colo., USA. References of interest regarding the IBM model 2997 channel centrifuge (and/or centrifuges like it) are U.S. Pat. Nos. 4,010,894, 4,094,461, 4,387,848 and 4,430,072 to Kellogg et al.; U.S. Pat. Nos. 4,386,730, 4,439,178, 4,447,221 and 4,708,712 to Mulzet; U.S. Pat. No. 4,647,279 to Mulzet et al.; U.S. Pat. No. 4,900,298 to Langley; U.S. Pat. No. 5,496,265 to Langley et al.; U.S. Pat. No. 4,850,995 to Tie et al.; U.S. Pat. No. 4,419,089 to Kolobow et al.; and the references cited within these patents.

The channel assembly 30 of FIG. 2 is in common use as a blood separator. Blood from a donor's arm is continuously pumped from a radially directed input line 32, through the inner channel wall 34, and into hollow channel 36 as the channel assembly 30 rotates. The various blood components (e.g., plasma and red blood cells) are flung toward the outer channel wall 38 by centrifugal force, and they therefore separate according to their specific gravity as the blood moves around channel from the input line 32 to several exit lines 40, 42, and 44 (shown in greater detail in FIG. 3). The blood cannot flow directly from the input line 32 to the output lines 40/42/44 and is forced to traverse the entirety of the channel 36 owing to the barrier 46 situated between the inlet and outlet lines 32 and 40/42/44. To collect the various layers of blood, the exit lines 40/42/44 are positioned at different radial locations spaced from the inner wall 34 of channel 36. Plasma, leukocytes (white cells), and red blood cells are each collected through respective exit lines 40, 42, and 44.

The structure and operation of continuous flow channel centrifuges may be better understood if they are compared and contrasted to the structure and operation of continuous flow bowl centrifuges. In the channel 36 of FIG. 2, blood flow is in an arcuate path centered about the rotational axis. Flow occurs entirely in planes perpendicular to the rotational axis, and the total length of the flow path subjected to centrifugal force of any appreciable magnitude is approximately 2 r (in the input and exit lines 32 and 40/42/44) plus 2 πr (in the channel 36), wherein r is the radial distance between the rotational axis and the inner wall 34 of the channel 36. The centrifugal force is exerted perpendicular to the channel 36, and most of the separation between heavy and light blood fractions occurs along its length, wherein the direction of blood flow is tangential to the channel 36 and in a direction perpendicular to the rotational axis.

In comparison, a continuous flow bowl-type centrifuge such as the one shown in FIG. 1 does not use a flow path curving about the rotational axis; rather, the flow path of any element of blood entering the centrifuge will be generally along a plane coincident with the rotational axis. The overall flow path has a length of 2 r plus h, the 2 r flow path being in the input and exit lines 24 and 26 and oriented in planes perpendicular to the rotational axis, and the h flow path being directed along the height of the bowl 22 and oriented in planes parallel to the rotational axis. Most of the separation between heavy and light blood fractions occurs along the walls of the bowl 22, wherein the direction of blood flow is generally parallel to the rotational axis.

A unique design feature of certain channel assemblies (such as the model 2997) is their rotating seal assembly 48. It consists of a stationary top half 50 and a bottom half 52 which rotates with the channel 36. The surfaces where the two halves 50 and 52 meet have four concentric matching grooves (not shown) that correspond to whole blood input line 32 and the three exit lines 40, 42, and 44. Whole blood and blood components are transferred from stationary to moving parts through the four grooves. The hydrodynamic design of the grooves and the viscosity of blood prevent the liquid from leaking between the junction of the two halves 50 and 52 of seal assembly 48, which is open to the atmosphere. Because bloodborne pathogens could potentially leak into or from the seal, blood cell separators using a rotating seal assembly have become obsolete.

Use of the Separation Channel to Concentrate Pathogenic Organisms

To concentrate pathogenic organisms from potentially contaminated food or water in accordance with the invention, the initial step is to prepare the food or water for supply to a channel assembly 30 such as the one illustrated in FIGS. 2 and 3, which is operated as a simple continuous-flow centrifuge. The food/water must have sufficient fluidity that it can be pumped into and out of the channel assembly 30, and where the food/water bears suspended particulate matter, the particles must be small enough that they will not clog the channel assembly 30. As reflected by the experimental results set out later in this disclosure, the channel assembly 30 has been proven to work well in concentrating pathogens from water having substantial turbidity (i.e., solids content), and thus water and fluid foods (e.g., beverages, yogurt, sauces, etc.) will generally not require any preliminary processing prior to sending them into the channel assembly 30. Highly viscous or solid foods, or foods bearing solid particles of greater size, may require preliminary treatment to suspend in a fluid medium those microorganisms embedded or entrapped within the food. Generally, this may be done by high-speed blending, filtration of coarse sediments, and/or by the addition of diluting water to prepare a fluid suspension of the food. In some cases, it may be sufficient to merely test fluid byproducts generated during food processing, e.g., rinsate from the washing of vegetables, animal carcasses, or other foods, excess fluids skimmed or drained from foods during manufacture or packaging, and so on. If the fluid is not fed to the channel 30 soon after it is obtained and pre-processed, it may be desirable to refrigerate it until it is ready for supply to the channel 30 to minimize interim growth and death of pathogens within the fluid.

Prior to sending the fluid through the channel 30, several other preliminary steps may be useful. First, the channel 36 and associated tubing are preferably primed with water containing a surfactant, for example 0.001% Tween 80 or Tween 20 (Sigma Chemical Co., St. Louis, Mo., USA), to enhance removal of the collected material containing the organisms after centrifugation is completed. Priming may be conducted with an output pump (not shown), the plasma pump built into the centrifuge, or a separate additional peristaltic pump (as discussed below). Priming with a surfactant is not performed if the channel assembly 30 is used for blood separation.

Second, when a centrifuge using the channel assembly 30 is used as a blood separator, donor safety sensors (not shown) within the centrifuge test the tubing of the channel assembly 30 for air emboli and pressure irregularities. When the channel assembly 30 is instead used to concentrate pathogenic organisms, the sensors and unnecessary pumps and circuits may be disabled or removed.

Third, when channel assemblies 30 having the split-seal arrangement 48 are used, water containing 50% glycerin (or another viscosity-modifying substance) may be pumped into the saline line (not shown) of rotating seal assembly 48 using a lubricant pump (not shown) operating at a speed of about 2.5 rpm. The glycerin creates a viscous barrier between water and air at the junction of the two halves 50 and 52 of seal assembly 48 to prevent leaking. Glycerin is not used when split-seal channel centrifuge assemblies are used as blood separators because blood is normally sufficiently viscous to move between stationary and moving halves 50 and 52 without leaking. If channel assemblies with newer valves (i.e., non-split-seal valves) are used, the viscosity modification is unnecessary.

The fluid potentially contaminated by pathogenic organisms is then fed into channel 36 via whole blood input line 32 at a suitable flow rate, generally in the range of between about 70 mL/min to 500 mL/min, and most preferably about 150 mL/min. The fluid is preferably centrifuged at a speed such that the relative gravitational force inside the channel 36 is at least 900×g, which equates to approximately 2400 rpm for the IBM model 2997 channel assembly 30. Centrifugation is performed for a period of time sufficient to process a predetermined sample volume. When determining an optimal flow rate and centrifugation speed, it is helpful to keep Stokes' equation in mind:

$$v = \frac{d^2(\rho_p - \rho_f)g}{18\mu}$$

where v=sedimentation rate
d=size (diameter) of particles to be concentrated
$p_p$=density of particles
$p_f$=density of liquid
$\mu$=viscosity of fluid medium
g=gravitational force (magnitude of centrifugal force field)

Stokes' equation establishes the following general propositions regarding centrifugation: (1) sedimentation is faster where the difference in density between the fluid medium and the particle is greater (and no sedimentation occurs where the particle density is equal to the density of the fluid medium); (2) sedimentation is faster where the gravitational force field is greater (i.e., where the centrifugation speed is greater); (3) sedimentation is faster where the particle size is larger; and (4) sedimentation is faster where the viscosity of the fluid medium is lesser. Beyond that, it is also evident that a longer period of centrifugation (e.g., a slower flow rate in a channel centrifuge) will enhance sedimentation.

Keeping these factors in mind, and noting that the potentially contaminated fluid will generally be aqueous in nature, it may in some cases be desirable to dilute the fluid medium with water to decrease its density and viscosity and thus enhance the sedimentation rate of pathogens. Further, where the pathogens of interest are smaller and/or less dense, increased centrifuge speeds and/or decreased flow rates will be of assistance in settling greater amounts of pathogens from the fluid. The densities of common food/waterborne pathogenic organisms (e.g., those listed at the outset of this disclosure) are generally greater than water, ranging between approximately 1.01–1.10 g/ml. The pathogenic protozoans generally range in size between approximately 1–15 µm, whereas the pathogenic bacteria are smaller, ranging from approximately 0.5–2 µm. However, it is notable that most of the aforementioned pathogenic organisms will often be found in water and fluid food in association with particles which are heavier than water (i.e., they bind or cling to such particles), particularly in the case of food particles. Therefore, in many cases, the size and density of the pathogens will not have a significant effect on organism recovery.

After centrifugation, the organisms and sediment (e.g., soil or food particles) are retained in channel 36 rather than being pumped out, as is customary with red blood cells when blood separation is performed. The supernatant is pumped out via plasma exit line 40, and the contents of channel 36 may then be tested by an appropriate method to determine the type and number of pathogenic organisms present. The channel contents can be accurately recovered by clamping the input and exit lines 32 and 40/42/44 from seal assembly 48 to channel 36, removing the channel 36 from the rotor, and draining its contents into a beaker. Superior recovery can be obtained by then cutting open the channel 36, rinsing it with water and/or a surfactant (e.g., 0.01% Tween 80), and combining the rinse(s) with the concentrate already recovered from the channel 36. Various test methods (e.g., immunofluorescence, nucleic acid detection via PCR or RT-PCR, fluorescent in situ hybridization, etc.) can then be used to test the concentrate for pathogens of interest. Commercially available kits for waterborne and foodborne pathogens are available from Meridian Diagnostics, Inc. (Cincinnati, Ohio, USA) (*E. coli,* Cryptosporidium, Giardia); BioControl Systems, Inc. (Bothell, Wash., USA) (*E. coli,* Listeria, Salmonella); BioMerieux Vitek, Inc. (Hazlewood, Mo., USA) (*E. coli,* Listeria); and IDEXX Inc. (Westbrook, Me., USA) (*E. coli,* coliform bacteria), as well as other suppliers. Alternatively, the concentrate can be sent to outside laboratories (preferably under refrigeration) for testing by standard or proprietary methods.

It is notable that apart from directly testing fluid for pathogens in the manner described above, the method can also be used to indirectly test for pathogens. As an example, in the meat industry, fluid from food streams to animals (and/or waste streams from animals) may be tested as well as (or instead of) meat from the animals themselves. This may indicate pathogen contamination of the animals and suggest possible preventive measures for destroying the pathogens before they are carried to later food processing steps. As another example, apart from testing fluid for pathogens per se, the fluid can instead (or also) be tested for "indicator organisms" which, when detected in food and water, indicate human and/or animal pollution of an intestinal origin. To illustrate, the coliform group of organisms are common inhabitants of the intestinal tract in humans and warm blooded animals, and have approximately the same behavior as the pathogenic bacteria Salmonella and Shigella. Thus, their presence in fluid indicates that Salmonella/Shigella contamination may be present, or at least that conditions are favorable for their maintenance. Other examples of indicator organisms include enterococci, which are good indicators of fecal contamination; *Clostridium perfringens,* which can itself cause food poisoning but which is relatively harmless (and common) in small amounts; and non-enteropathogenic strains of *E. coli.*

Experimental Results

Initial experiments to test the feasibility of channel assembly 30 for concentrating and collecting pathogenic organisms from water will now be summarized. An aqueous medium was spiked with a pathogen at a known concentration. The chosen pathogens were Cryptosporidium and *Escherichia coli,* which are respectively near the upper and lower size/weight ranges for food- and waterborne pathogens and thus should respectively represent lesser and greater concentration difficulty. The medium was then centrifuged by use of a continuous flow channel centrifuge. Except for experiments 6, 7 and 8 summarized below, the aforementioned model 2997 channel assembly 30 was used.

Several tests were conducted at the maximum sample feed rate of the built-in plasma pump, about 70 mL/min. Other tests used a separate peristaltic pump which was not part of channel assembly 30 and which was capable of providing a maximum sample flow rate of 500 mL/min. Centrifugation took a few minutes to several hours depending on the water sample volume. The processing time is normally calculated as the sample volume divided by the sample feed rate, and in general, the centrifugation time necessary to concentrate protozoa from typical water samples will be on the order of about ½ to 4 hours when the model 2997 channel assembly 30 is used. For smaller samples, lesser times are sufficient.

After centrifugation was complete, the input and exit lines 32 and 40/42/44 from seal assembly 48 to channel 36 were carefully clamped, the channel 36 removed from the rotor, and the contents drained into a beaker. The channel 36 was carefully cut in half so that its contents were not spilled, and its cut ends were then clamped with VISE GRIP pliers. Each half of the channel 36 was then filled with 0.01% Tween 80 and its ends were clamped shut. The channel 36 was then shaken vigorously and placed on a laboratory vortex to dislodge any organisms that may have adhered to the channel. This rinsing procedure was conducted several times. The concentrate and all rinses were combined. For these feasibility studies, no further steps were taken to separate organisms from solids in the fluid.

In the below tests involving Cryptosporidium, the combined concentrate and rinses were then examined for oocysts by use of the Merifluour Detection Kit, an immunofluorescent assay produced by Meridian Diagnostics, Cincinnati, Ohio. All results are reported as percent recovery, i.e. total number of organisms recovered in the channel divided by the number added to the medium, multiplied by 100.

EXPERIMENT 1: Recovery of Cryptosporidium Oocysts from Phosphate-Buffered Saline Solution Phosphate-buffered saline (PBS) is a simpler aqueous medium than naturally occurring surface or ground water, and therefore would presumably present optimum conditions for concentrating Cryptosporidium oocysts by a continuous flow channel centrifuge. Apart from testing oocyst recovery at these theoretically optimum conditions, the experiment tested whether recovery efficiency varied with oocyst concentration, an important consideration given the range of oocyst densities that exist in the environment.

Cryptosporidium oocysts from the positive control of the Merifluour Detection Kit were diluted with 10% formalin to make a working stock solution having a concentration of approximately 5000 oocysts/mL. Oocysts were spiked into 2 or 5 L of PBS to achieve the following four target concentrations: 1000, 100, 20 or 5 oocysts/L. The IBM 2997 blood cell separator was used as the continuous flow channel centrifuge. The centrifuge feed rate was set at 70 ml/min, and the rotor speed was 2200 rpm (relative centrifugal force of 740×g). The total centrifuge time was ½ to 1 hour per sample. The recovery efficiency of the centrifuge was tested 3 to 5 times at each oocyst concentration.

The material from the channel was tested for oocyst presence. The supernatant remaining in the channel after centrifugation was also collected, concentrated by bulk centrifugation at 10000×g for 15 min, and the pellets were analyzed for oocysts in the same manner. The results show that Cryptosporidium recoveries of greater than 69% were achieved, and that, most importantly, a recovery of nearly 100% was achieved for the most dilute oocyst concentration (5 oocysts/L):

| Oocysts/Liter | No. of Tests | Mean % Recovery | Std. Dev. % Recovery |
|---|---|---|---|
| 100 | 3 | 84.4 | 15.7 |
| 1000 | 4 | 68.5 | 5.7 |
| 20 | 5 | 93.8 | 33.0 |
| 5 | 3 | 98.8 | 16.7 |

EXPERIMENT 2: Recovery of Cryptosporidium Oocysts from Pond Water

To more closely simulate the conditions under which the invention would operate when concentrating naturally occurring Cryptosporidium, live oocysts were spiked into pond water. Recovery efficiencies were compared with those attained using PBS and between two oocyst concentrations in pond water.

Purified live Cryptosporidium oocysts were obtained from Parasitology Research Labs (Phoenix, Ariz., USA) and diluted with distilled water for a working stock concentration of approximately 15,000 oocysts/mL. Oocysts were spiked by adding the appropriate volume of stock solution to 100 mL of pond water, fixing the Cryptosporidium with formalin (10% final concentration), then mixing the 100 mL aliquot in the larger pond water volume to be centrifuged. These steps were taken to insure that the organisms were killed while minimizing the amount of added formalin.

Cryptosporidium oocysts were spiked into 2, 10, or 15 liters of pond water, collected from the same local pond (Pond 1) on the day of centrifugation. Water was collected from the pond surface with 5 gallon buckets where the water depth was at least 50 cm. Collection of bottom sediments was avoided. The sampled pond water had 49 mg/L total solids and turbidity of 2.1 NTU.

Ten liters of water from Pond 1, without added oocysts, were centrifuged as a control. Indigenous Cryptosporidium oocysts were not found. Oocyst target concentrations were 1000 or 100 oocysts/L. The centrifuge feed rate was set at 70 mL/min, and the rotor speed was 2400 rpm (generating approximately 900×g of force). Centrifuge times were ½ to 3½ hours. The recovery efficiency was tested 3 times at each oocyst concentration.

The results, presented below, show recoveries of 100% for the most dilute oocyst concentration (100 oocysts/L). The percentage recoveries were calculated based on the concentration of oocysts retained in the channel as compared to the amount of the initial spiking. The supernatants were also examined for oocysts not retained by the centrifuge. No oocysts were detected in any of the supernatants. Thus, it is most likely that organism separation in the channel was close to 100%, and the apparent loss of organisms from the concentrate to be tested probably arises due to other steps in the process (e.g., during use of the immunofluorescent assay).

| Oocysts/Liter | No. of Tests | Mean % Recovery | Std. Dev. % Recovery |
|---|---|---|---|
| 100 | 3 | 102.9 | 5.6 |
| 1000 | 3 | 90.3 | 10.8 |

EXPERIMENT 3: Recovery of Cryptosporidium Oocysts as a Function of Sample Feed Rate The time required to concentrate oocysts by continuous flow centrifugation depends on the sample volume and the sample feed rate into the centrifuge. Given the maximum relative centrifugal force generated by the blood cell separator (900×g), this experiment was conducted to determine the maximum sample feed rate that could be used without reducing recovery efficiency.

Purified live Cryptosporidium oocysts were used as described in Experiment 2. Cryptosporidium oocysts were spiked into 2 or 10 L of water from Pond 1. The target concentration of oocysts was 1000/L for all centrifugation runs. Percent recovery was measured at three sample feed rates: 150, 250, and 500 ml/min. Centrifugation times were several minutes to 1 hour.

Samples were pulled into the channel at the desired rate by a peristaltic pump (Cole Parmer model 7553-20) placed downstream from the channel. The built-in centrifuge pumps were bypassed because their maximum pumping rate is only 70 ml/min. Recovery efficiencies were measured 3, 4 or 5 times at each sample feed rate.

The results, presented below, show recovery rates of between 45–95%, with the highest recovery achieved at the lowest flow rate tested (150 mL/min). Oocysts were found in the supernatant when the flow rates were 250 and 500 mL/min.

| Pump Speed mL/min | No. of Tests | Mean % Recovery | Std. Dev. % Recovery |
|---|---|---|---|
| 150 | 3 | 94.4 | 5.9 |
| 250 | 3 | 70.3 | 6.0 |
| 500 | 5 | 43.3 | 5.5 |

EXPERIMENT 4: Recovery of Cryptosporidium From Pond Water, Sample Feed Rate=150 mL/min Having observed in Experiment 3 that oocysts could be recovered efficiently when the sample feed rate is 150 mL/min, this example tested whether the recovery efficiency changed with oocyst concentration at that feed rate.

Purified live Cryptosporidium oocysts were used as described in Experiment 2. Cryptosporidium oocysts were spiked into 10 or 25 L of water from another local pond, here denoted Pond 2. For Pond 2, total solids were 182 mg/L, and turbidity was 8.3 NTU.

Ten liters of water from Pond 2 without added oocysts was centrifuged as a control. Indigenous Cryptosporidium oocysts were not found.

Target concentrations were 1000, 100 or 20 oocysts/L. The independent peristaltic pump pulled the samples into the IBM 2997 centrifuge at a flow rate of 150 mL/min. The rotor speed was 2400 rpm (900×g). The time for centrifugation was one to three hours. Recovery efficiencies were measured 3 or 4 times at each Cryptosporidium concentration.

Supernatants were tested as described in Experiment 1. The results, presented below, show Cryptosporidium recoveries of between 80% and nearly 100%, with the highest recovery achieved at an oocyst concentration of 100 oocysts/L.

| Oocysts/Liter | No. of Tests | Mean % Recovery | Std. Dev. % Recovery |
|---|---|---|---|
| 100 | 4 | 100.8 | 15.1 |
| 1000 | 3 | 97.2 | 9.6 |
| 20 | 3 | 77.9 | 17.9 |

EXPERIMENT 5: Recovery of Giardia Cysts From Pond Water

The centrifugation process was tested with Giardia lamblia, another waterborne protozoan pathogen, to assess whether the centrifuge could efficiently concentrate pathogens larger than Cryptosporidium.

Purified live Giardia cysts were obtained from Parasitology Research Labs (Phoenix, Ariz., USA) and diluted with distilled water to approximately 22,000 cysts/mL. Cysts were added to water from Pond 2 following the same procedure for Cryptosporidium described in Experiment 2.

Ten liters of water from Pond 2, without added cysts, were centrifuged as a control. Indigenous Giardia cysts were not found. Giardia cysts were spiked into 10 or 30 L of pond water. Target concentrations of Giardia cysts were 1000, 100 or 20/L. The centrifuge setup was the same as described in Experiment 4. Sample feed rate was 150 mL/min, and the rotor speed was 2400 rpm. Centrifuge time was 1 to 3½ hours. Recovery efficiencies were measured 3 times at each Giardia concentration.

The results, presented below, show recoveries of Giardia cysts to be between 90–100%.

| Target Concentration Oocysts/Liter | No. of Tests | Mean % Recovery | Std. Dev. % Recovery |
|---|---|---|---|
| 100 | 3 | 94.6 | 5.2 |
| 1000 | 3 | 104.2 | 5.7 |
| 20 | 3 | 97.0 | 10.5 |

EXPERIMENT 6: COBE Spectra Centrifuge

The COBE Spectra centrifuge is a newer continuous flow channel centrifuge for use in blood cell separation. Unlike the IBM 2997 centrifuge discussed above, there is no rotating ceramic seal. The channel itself has a hoop-shaped geometry similar to the channel 36 of FIG. 2.

Purified live Cryptosporidium oocysts were used as described in Experiment 2. Oocysts were spiked into 5 or 7.5 L of water from Pond 2. The oocyst target concentration was 100/L for all centrifuge runs. The input pump of the COBE Spectra centrifuge was set at 150 mL/min, and the rotor speed was 2400 rpm (900×g). The recovery efficiency was tested 3 times.

Using the COBE centrifuge to concentrate Cryptosporidium, 100% of the spiked Cryptosporidium oocysts were recovered.

| Oocysts/Liter | No. of Tests | Mean % Recovery | Std. Dev. % Recovery |
|---|---|---|---|
| 100 | 3 | 103.3 | 14.8 |

EXPERIMENT 7: Recovery of Cryptosporidium Oocysts as a Function of Water Turbidity An effective method for concentrating pathogenic organisms from water must work over a wide range in water turbidity. In this experiment turbidity was manipulated by concentrating seston in pond water by bulk centrifugation (10,000×g for 15 minutes). For example, to increase turbidity 10-fold above ambient, 10 volumes of pond water were concentrated and the seston pellets added and mixed to the unit volume to be spiked with oocysts. Turbidity was measured using a fluorescence spectrophotometer (Hitachi Model F-4500, excitation and emission wavelengths=500.0 nm, slit width=2.5 nm, and PMT voltage=400 V). Oocysts were spiked into 7.5 L pond water, as described in Experiment 2, at a target concentration of 100 oocysts/L. Oocysts were recovered with the COBE Spectra centrifuge (rotor speed=2400 rpm or approximately 900×g, sample feed rate=150 mL/min).

The results, presented below, show that percent recovery of oocysts did not vary with turbidity levels between 2.6 and 30.8 NTU (F statistic, p>0.05, comparison based on count aliquots (n=6) because turbidity levels could not be replicated).

| Turbidity (NTU) | No. of Aliquot Counts | Mean % Recovery | Std. Dev. % Recovery |
|---|---|---|---|
| 2.6 | 6 | 84.9 | 17.0 |
| 4.8 | 6 | 81.5 | 27.7 |
| 8.6 | 6 | 92.2 | 20.1 |
| 15.7 | 6 | 93.8 | 29.9 |
| 20.1 | 6 | 101.2 | 40.9 |
| 30.8 | 6 | 82.3 | 29.3 |

EXPERIMENT 8: Recovery of Cryptosporidium from Large Pond Water Volumes

Given that waterborne pathogenic organisms may occur in dilute densities, an effective concentration method must be able to process a large sample volume, on the order of 100 liters. In this experiment live and purified Cryptosporidium oocysts were spiked into 100 L of pond water. Spiking was conducted as described for Experiment 2. The target density was 100 oocysts/L. Oocysts were recovered with the COBE Spectra centrifuge (rotor speed=2400 rpm or approximately 900×g, sample feed rate=150 mL/min). Centrifugation time for this rotor speed and sample feed rate was 11 hours.

Mean percent recovery of Cryptosporidium oocysts from 100 L of pond water was 94.7±9.7% (mean±1 standard deviation, n=3). The recovery efficiency was not significantly different than recovery with the centrifuge and a sample volume of 5 to 7 L (two-tailed t test, p>0.05), as performed in Experiment 6.

EXPERIMENT 9: Recovery of *Escherichia coli* from Phosphate-Buffered Saline Solution Three experiments were conducted to evaluate the efficiency of aforementioned IBM 2997 channel assembly 30 for concentrating the foodborne bacterium *Escherichia coli*. Ten L phosphate-buffered saline (PBS, pH 7.4) was purified by filtering twice (0.2 $\mu$m filters) to remove contaminating bacteria. *E. coli* was then seeded live into the PBS at 10,000 cells/L. Continuous centrifugation was conducted at 2400 rpm (equating to approximately 900×g), the maximum speed of the COBE Spectra centrifuge, with a flow rate through the channel of 70 mL/min.

After centrifugation, bacteria were enumerated by separately filtering the approximately 200 mL of concentrate (the PBS in the channel after centrifugation) and 500 mL of supernatant (the PBS passed through the channel) through 0.2 $\mu$m pre-blackened polycarbonate membranes (25 mm diameter) and staining with BacLight (Molecular Probes, Eugene, Oreg., USA). The following bacteria counts were obtained:

| | |
|---|---|
| Trial 1: | 89,053 cells in concentrate (0.18 L, 494,739 cells/L) |
| | 365,956 cells in supernatant (9.8 L, 37,342 cells/L) |
| Trial 2: | 52,196 cells in concentrate (0.125 L, 417,568 cells/L) |
| | 167,209 cells in supernatant (8.3 L, 20,146 cells/L) |
| Trial 3: | 61,486 cells in concentrate (0.12 L, 512,383 cells/L) |
| | 142,380 cells in supernatant (7.5 L, 18,984 cells/L) |

The number of bacteria present after centrifugation was greater than the number added, indicating that the live bacteria were multiplying during centrifugation. A mass balance approach for calculating recovery efficiency (percent recovery) is thus appropriate, with recovery efficiency being calculated as the number of *E. coli* in the concentrate divided by the sum of *E. coli* in the concentrate and supernatant, multiplied by 100. The three replicate trials respectively produced recovery efficiencies of 19.6%, 23.8%, and 30.2%, providing an average recovery efficiency of 25%±5% (±1 standard deviation).

While this recovery efficiency is not as great as those reflected in the Cryptosporidium experiments above, it clearly illustrates that the invention provides a valuable alternative to the time-consuming enrichment steps which are commonly used to concentrate bacterial pathogens prior to their detection and measurement. Thus, the invention could replace the standard enrichment steps to eliminate the long delay (and much of the expense) in testing food/water for bacterial pathogens.

It should also be noted that bacteria recovery efficiencies in fluid food can be expected to be higher than those obtained in purified PBS. This is because in fluid food samples, bacteria generally cling to food particles. These food particles, which are often larger and heavier than even the protozoan parasites, settle quite readily during centrifugation. Depending on the food type, they will not significantly interfere with pathogen detection and measurement. Bacteria will often tend to associate with particulate matter suspended in water as well.

It is expected that if the COBE Spectra centrifuge was capable of higher speed (and thus generating greater centrifugal force), higher recoveries could be obtained. With Stokes' equation in mind, extrapolation of the experimental results given above suggests that *E. coli* recoveries around 100% would be obtained at approximately 9600 rpm (3600× g). Construction or modification of a channel centrifuge which reaches speeds of this magnitude or higher is technically feasible with the application of ordinary engineering skill. However, no channel centrifuges reaching this speed are currently marketed, likely because channel centrifuges have heretofore been devoted to blood component separation and speeds on the order of 2400 rpm are more than adequate for this application. Apart from increased centrifugation speed, other means of enhancing recovery efficiency noted elsewhere in this disclosure could also be used, such as by decreasing the flow rate.

Finally, it is also noted that if it is desirable to hinder the growth of organisms during centrifugation, the organism-bearing fluid could be refrigerated prior to, during, and/or after centrifugation, as by situating the channel within a refrigerated chamber during centrifugation and/or refrigerating the input/exit lines to the channel.

Modifications and Alternate Embodiments

Figure 4:
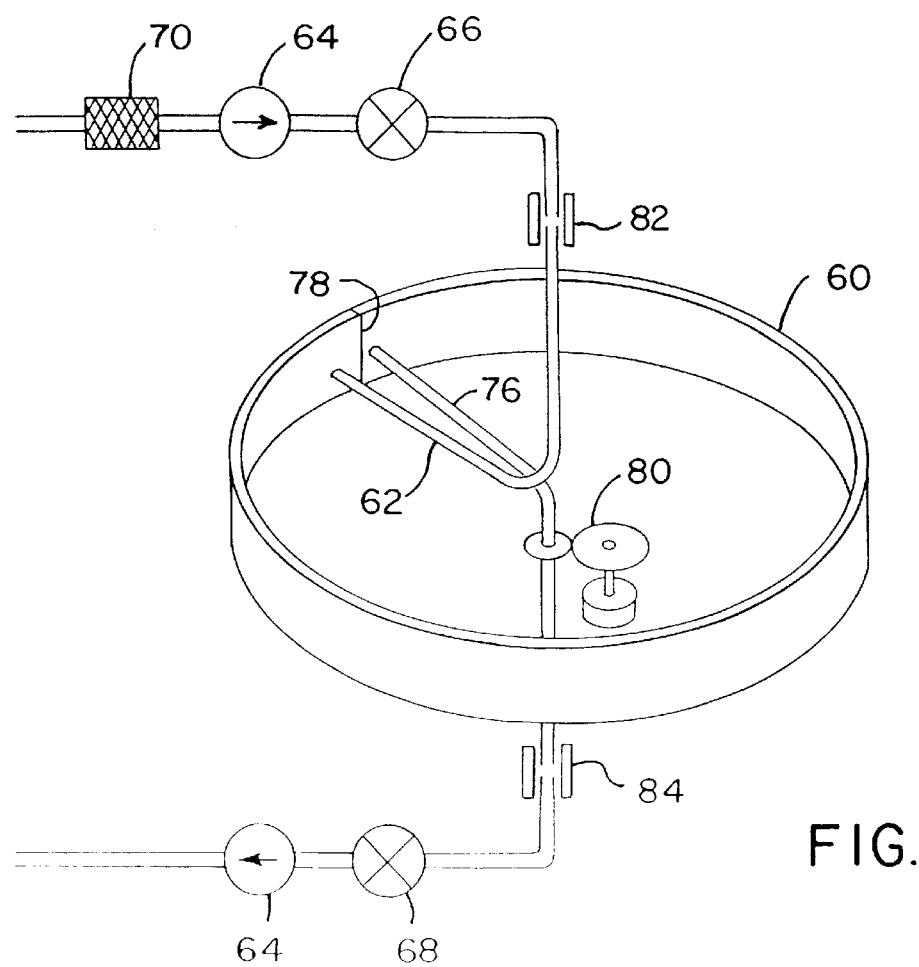
Figure 5:
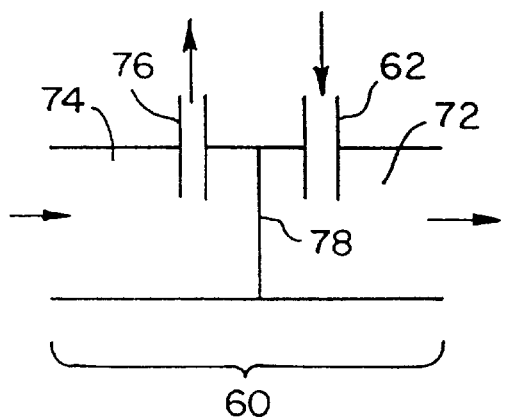

Another embodiment of a channel suitable for use in concentrating dilute densities of pathogenic organisms from fluid is illustrated in FIGS. 4 and 5. The channel 60 includes an input line 62 downstream of a pumping means 64 for supplying potentially contaminated fluid to the channel 60. This pumping means 64 is a source of static or dynamic pressure head, i.e., a pump, tank, or other fluid sources which generate fluid flow into the input line 62. Pressure restriction/flow control valves can be provided upstream and/or downstream of the channel 60, as illustrated at 66 and 68. A coarse sediment filter 70 may also be placed upstream from the channel 60 to remove any gross impurities from the input line 62 before they enter the channel 60 and clog it. Fluid flows from the input line 62, into the channel entry 72, and then through the channel 60 (not fully shown in FIG. 5) to the channel end 74. The fluid then exits the channel 60 from the exit line 76, which may have a downstream pumping means in addition to (or in place of) the pumping means 64 upstream of the input line 62. As shown in FIG. 5, the channel end 74 and channel entry 72 are separated by a barrier 78 so that fluid can only reach the exit line 76 from the input line 62 after flowing through the entirety of the channel 60. The centrifuge drive is depicted at 80. The principal difference between the apparatus of FIGS. 4 and 5 from that of FIGS. 2 and 3 is that the channel 60 need only include a single exit line 76 rather than several, since separation of the input fluid into multiple fractions of different density will generally not be of interest. Additionally, the split-seal valving arrangement (and thus the necessity for adding a viscosity modifier) is avoided by having the input and exit lines 62 and 76 extend axially to join high-speed rotary seals 82 and 84.

Figure 6:
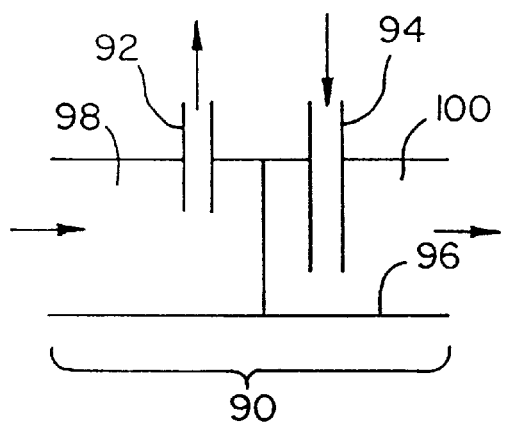
Figure 7:
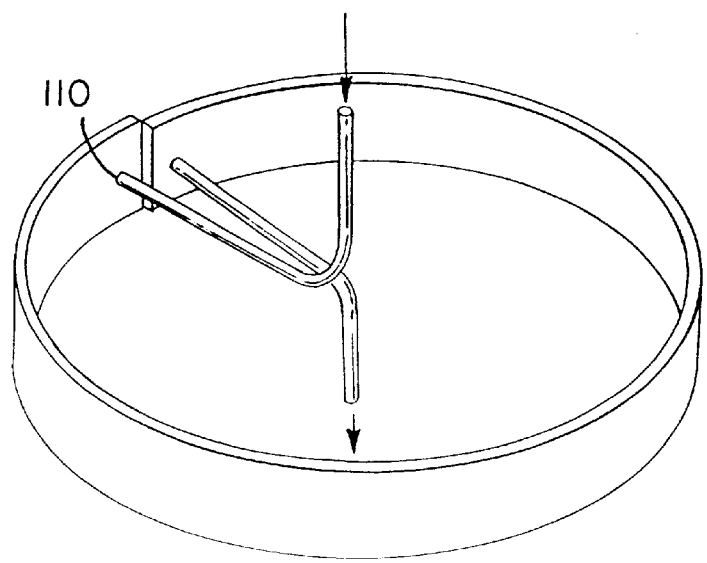

Another embodiment of a channel suitable for use in concentrating dilute densities of pathogenic organisms from fluid is illustrated in FIG. 6. The channel 90 of FIG. 6 differs from that of FIGS. 2–3 in several important respects. First, it need only include a single exit line 92 rather than several. Second, the input line 94 is located radially outward of the exit line 92, rather than at a radially inward or radially equivalent position. The use of a radially inwardly located exit line 92 helps to prevent organisms from being carried directly to the input line 94 to the exit line 92 by the fluid flow, or from being diverted to the exit line 92 due to turbulence in the channel, because the organisms will be more likely to settle radially outwardly to the outer channel wall 96 by the time they reach the channel end 98. In other words, immediately upon entering the channel entry 100 via the input line 94, the heavier organisms will begin traveling toward the outer channel wall 96 and are less likely to defeat the force gradient to exit the exit line 92. The input line 94 can be radially positioned inward of the exit line 92 by simply fixing the input and exit lines 94 and 92 in this location, as shown in FIG. 6. Alternatively (or additionally), this is done by modifying the shape of the channel so that the channel end 98 is located radially inward of the channel entry 100, as by modifying the channel into a generally spiral shape rather than an annular shape. In this configuration, which is shown in FIG. 7, the highest centrifugal force vectors are exerted on the organisms near the channel entry 110.

Figure 8:
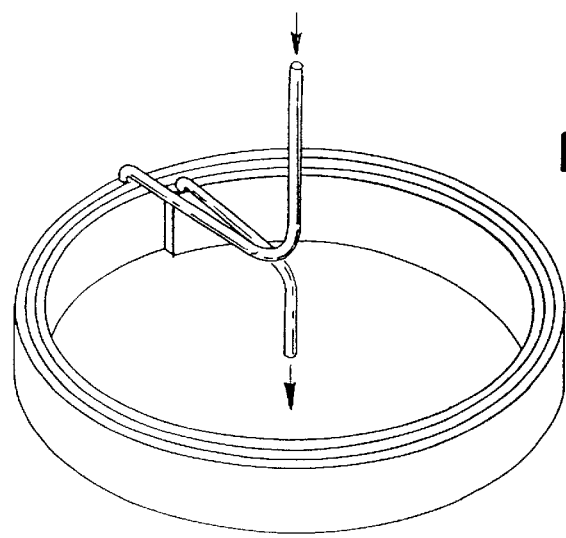
Figure 9:
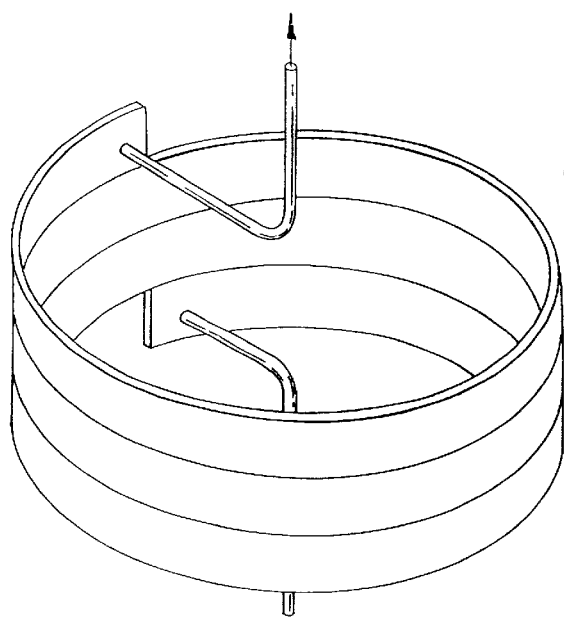

Regarding the modification of the channel into a spiral shape, it is noted that embodiments such as that of FIG. 8 are possible wherein a horizontal spiraling configuration allows for a channel of much greater length, and thus much greater residence time for the fluid flowing therein. The vertical spiraling configuration of FIG. 9 is another possibility. The longer channels provided by these embodiments may help in further concentration of organisms.

Figure 10:
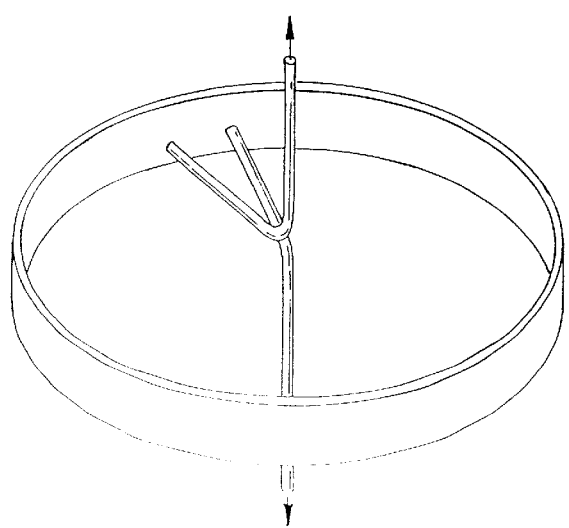

It is also possible to modify the shape of the channel into a generally elliptical configuration, as shown in FIG. 10. Configurations of this type may be helpful in that higher concentrations of organisms may gather at the areas wherein the channel intersects the major axes of the ellipse, since these are the areas where the maximum centrifugal forces are exerted on the fluid.

Figure 11:
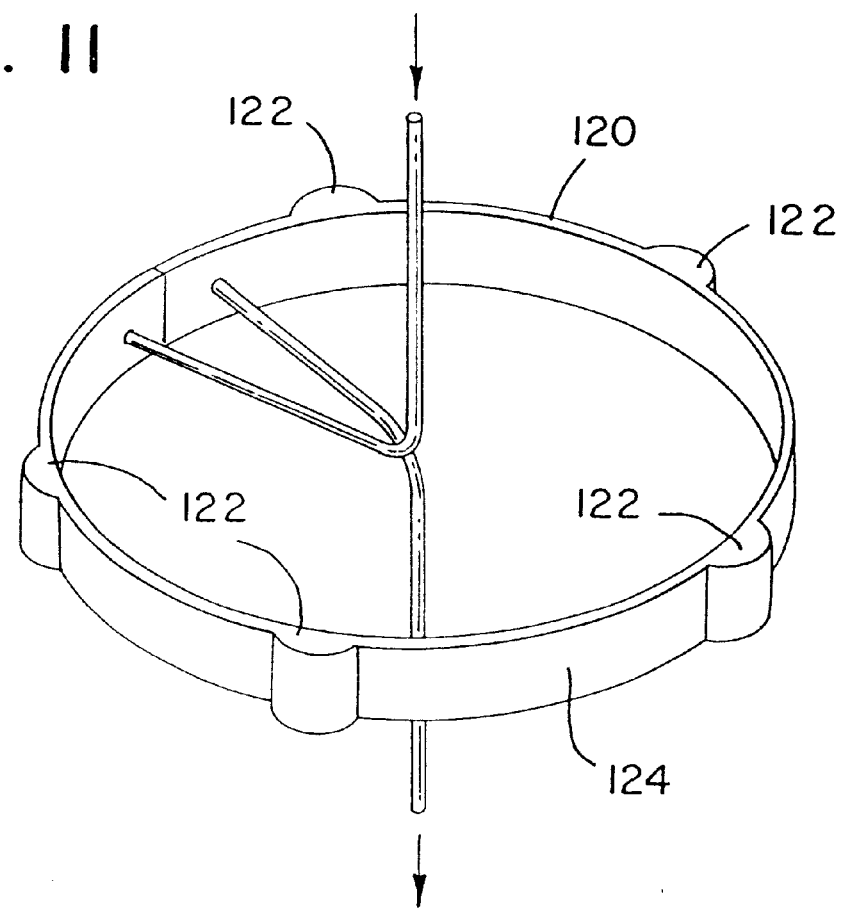

In similar fashion, it may be helpful to form a series of depressions in the outer wall of the channel, as exemplified in the channel 120 of FIG. 11. These depressions form traps 122 which may catch and retain organisms to a greater degree than the surrounding regions on the outer channel wall 124, which are located more radially inward.

Figure 12:
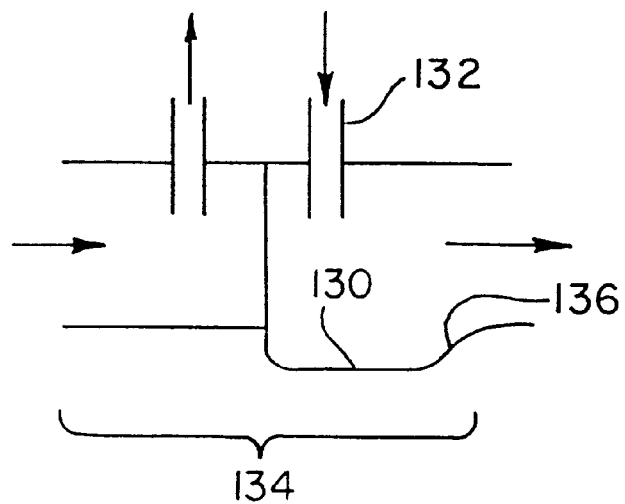

Strategic placement of these traps may lead to other beneficial results as well. As an example, FIG. 12 provides a closer view of a trap 130 opposite the input line 132. A trap 130 at or near this location is recommended when more turbid fluid is being tested, not so much for the purpose of capturing organisms, but for capture of sand and other very heavy detritus. Upon entering the channel 134, these heavy gross impurities will rapidly fall into the trap 130, thus providing for "cleaner" collection of organisms in downstream channel areas. However, if any traps 130 or other discontinuities are formed in any of the walls of the channel 134, care must be taken to form them in such a manner that they do not generate undue turbulence in the fluid flow (hence the gently sloping downstream surface 136 of the trap 130 shown in FIG. 12). Such turbulence may dislodge organisms from the channel walls or redivert a settling organism into a flow path located further radially inward, and this could result in organisms escaping the channel 134.

It may also be helpful to form the aforementioned traps 130/136 with transparent walls so that the contents of the traps 130/136 will be visible to centrifuge operators when the channel is at rest. Such traps would also be visible when the channel is spinning if used in conjunction with a strobe.

Recoveries of microorganisms might also be increased if the aforementioned channels are coated with (or formed of) materials which retain the microorganisms by chemical, electrostatic, or other forms of attraction. As an example, the interior walls of channels could be coated with antibodies specific to the microorganism(s) of interest. As another example, channels could be charged so that oppositely-charged microorganisms will be attracted to the channel walls and retained thereon. In similar fashion, the supernatant could be pumped through a filter (charged or otherwise) to capture microorganisms that escaped retention in the channel. It is notable that without the prior centrifugation step, filtration would in many cases be ineffective since the filters would rapidly clog. However, with prior centrifugation, coarse sediment is captured prior to entering the filter, thereby making filtration feasible.

It is noted that while the invention has generally been described with reference to a channel having a duct-like fully enclosed flow passageway, the channels described in this disclosure are not confined to this form. Consider, for example, that the inner channel wall 34 of the channel 36 of FIGS. 2 and 3 is not absolutely necessary if fluid addition, fluid withdrawal, and channel flushing all occur while the channel 36 is rotating at high speed: since the liquid is flung radially outward against the outer channel wall 38 by centrifugal force, the inner channel wall 34 would not restrain the liquid or have any other practical effect on the liquid. Similarly, the overall shape of the channel—whether circular, elliptical, or spiral, and whether oriented entirely within the same plane or in multiple planes (as in the vertical spiral configuration illustrated in FIG. 9)—is not critical, though it can provide desirable results if properly chosen. What is regarded to be important is the introduction of potentially-contaminated fluid into a continuous flow centrifuge wherein the flow is generally tangentially oriented over at least a section of the flow path. (In this disclosure, when a section of a flow path is stated to have "tangential" or "tangentially oriented" flow, this is intended to mean that when this section of the flow path is viewed from a direction coincident with the rotational axis, the instantaneous direction of liquid flow at each location along the section is at least substantially coincident with or parallel to the instantaneous direction of motion of the liquid at that location owing to rotation. As an example, the hoop-like channel of FIG. 2 has tangential flow.) In a continuous flow centrifuge utilizing generally tangential flow, this is best met by situating the input and exit lines substantially near the ends of the flow path. Thus, the optimal hoop-shaped channel for use in concentrating pathogenic organisms would use closely-spaced input and exit lines connected to the channel, with the channel having a barrier between the input and exit lines to force the fluid to flow through the full extent of the channel. Such a barrier need not fully close the channel; rather, it need only extend radially inward from the outer channel wall to such an extent that the fluid, when input at a given flow rate and when subjected to centrifugal forces, resides at a height lower than the height of the barrier (this "height" being measured in the radial direction).

However, there is a factor that is regarded to be of potential importance regarding the form of the channel. It is believed that forming the channel to better maintain laminar flow conditions therein, as by removing any sharp convergences, divergences, or discontinuities within the channel, will result in better recovery of organisms. Turbulence may allow the organisms to defeat centrifugal force gradients within the channel and allow the organisms to escape the channel's exit line. Laminar flow may also be encouraged by maintaining a lower flow rate through the channel, though higher flow rates are of course preferred for obtaining lesser testing times with larger sample throughput.

As noted above, it is believed that longer channels (flow paths) are believed to yield better organism recovery. However, it is conceivable to have a channel with a shorter flow path than the channels described above, as in the case of a channel which occupies only a subsection (arc) of a path curving about the rotational axis, or a circular channel wherein the inlet and exit lines are spaced apart with no barrier situated between so that two shorter flow paths are effectively formed, each having an opposite flow direction. While these would likely result in at least partial recovery of organisms, it is believed that they would not attain the same degree of recovery as a standard hoop-like channel operating under similar conditions. It is suggested in any case that channels used in accordance with the invention have flow paths with lengths greater than 2 r, where r is the radial distance from the rotational axis to the inner wall of the channel, and preferably a length approaching 2 πr. In the case of spiral, elliptical, or other noncircular channels, this relationship is interpreted to have r be the average of the maximum and minimum radial distances from the rotational axis to the inner wall of the channel.

At some point, it may be desirable to concentrate pathogenic organisms which have a density lower than the mean density of the fluid wherein they are borne, as where the organisms have accumulated large amounts of intracellular lipids. In this case, the teachings set out above may still be applied with thought being given to the result to be achieved; for example, the input/exit line arrangement of FIG. 6 may be modified to have the input line located radially inward of the exit line, the traps of FIGS. 11 and 12 may be located on the inner channel wall rather than the outer channel wall, and so on.

It is understood that preferred embodiments of the invention have been described above in order to illustrate how to make and use the invention. The invention is not intended to be limited to these embodiments, but rather is intended to be limited only by the claims set out below. Thus, the invention encompasses all alternate embodiments that fall literally or equivalently within the scope of these claims. It is understood that in the claims, means plus function clauses are intended to encompass the structures described above as performing their recited function, and also both structural equivalents and equivalent structures. As an example, though a nail and a screw may not be structural equivalents insofar as a nail employs a cylindrical surface to secure parts together whereas a screw employs a helical surface, in the context of fastening parts, a nail and a screw are equivalent structures.

What is claimed is:

1. A method of concentrating microorganisms from fluid comprising the steps of:
   a. continuously feeding the fluid into an elongated flow path, the flow path including a separation section wherein the fluid flows in an arcuate path about a rotational axis in directions which are substantially tangential with respect to the rotational axis, the separation section having a length greater than 2 r, where r is the average of the maximum and minimum radial distances of the flow path from the rotational axis; and
   b. subjecting the flow path to centrifugal forces by spinning the flow path about the rotational axis, wherein the centrifugal forces are substantially perpendicular to the separation section.

2. The method of claim 1 wherein after spinning the flow path, at least a portion of the fluid therein is tested for the presence of pathogenic organisms.

3. The method of claim 1 wherein the surfaces defining the flow path are at least partially coated with a surfactant.

4. The method of claim 1 wherein the flow path includes a fluid input line and a fluid exit line, each situated near an end of the flow path.

5. The method of claim 4 wherein the input and exit lines are adjacent each other on the flow path with a barrier resting therebetween.

6. The method of claim 4 wherein at least one of the input and exit lines is substantially radially oriented toward the rotational axis.

7. The method of claim 1 wherein the separation section includes the point on the flow path which is spaced at the maximum radial extent from the rotational axis.

8. The method of claim 1 wherein the separation section has a length greater than 2 πr.

9. The method of claim 1 wherein the flow path is defined by a channel centrifuge.

10. The method of claim 1 wherein the fluid is filtered after centrifugation.

11. A method of concentrating microorganisms from fluid comprising the steps of:
    a. continuously feeding the fluid into an elongated flow path, the flow path including a separation section wherein the fluid flow is oriented in directions substantially tangential with respect to a rotational axis; and
    b. subjecting the flow path to centrifugal forces by spinning the flow path about the rotational axis, wherein the centrifugal force is substantially perpendicular to the separation section.

12. The method of claim 11 wherein after spinning, at least a portion of the fluid in the flow path is tested for the presence of pathogenic organisms.

13. The method of claim 11 wherein the surfaces defining the flow path are at least partially coated with a surfactant.

14. The method of claim 11 wherein the separation section follows an arcuate path defined about the rotational axis.

15. The method of claim 11 wherein the flow path includes a fluid input line and a fluid exit line, each situated near an end of the flow path.

16. The method of claim 15 wherein the input and exit lines are adjacent each other on the flow path with a barrier resting therebetween.

17. The method of claim 15 wherein at least one of the input and exit lines is substantially radially oriented toward the rotational axis.

18. The method of claim 11 wherein the separation section includes the point on the flow path which is spaced at the maximum radial extent from the rotational axis.

19. The method of claim 11 wherein the separation section has a length greater than 2 r, where r is the average of the maximum and minimum radial distances of the flow path from the rotational axis.

20. The method of claim 19 wherein the separation section has a length greater than 2 πr.

21. The method of claim 11 wherein the flow path is defined by a channel centrifuge.

22. The method of claim 11 wherein the fluid is filtered after centrifugation.

23. A method of concentrating microorganisms from fluid comprising the steps of:
   a. continuously feeding the fluid into an elongated flow path, the flow path including a separation section wherein the fluid flows in an arcuate path about a rotational axis; and
   b. subjecting the flow path to centrifugal forces by spinning the flow path about the rotational axis, wherein the centrifugal force is substantially perpendicular to the separation section.

24. The method of claim 23 wherein after spinning the flow path, at least a portion of the fluid therein is tested for the presence of pathogenic organisms.

25. The method of claim 23 wherein the surfaces defining the flow path are at least partially coated with a surfactant.

26. The method of claim 23 wherein the flow path includes a fluid input line and a fluid exit line, each situated near an end of the flow path.

27. The method of claim 26 wherein the fluid input and exit lines are adjacent each other on the flow path with a barrier resting therebetween.

28. The method of claim 26 wherein at least one of the input and exit lines is substantially radially oriented toward the rotational axis.

29. The method of claim 23 wherein the separation section includes the point on the flow path which is spaced at the maximum radial extent from the rotational axis.

30. The method of claim 23 wherein the separation section has a length greater than 2 r, where r is the average of the maximum and minimum radial distances of the flow path from the rotational axis.

31. The method of claim 30 wherein the separation section has a length greater than 2 πr.

32. The method of claim 23 wherein the flow path is defined by a channel centrifuge.

33. The method of claim 23 wherein the fluid is filtered after centrifugation.

34. A method of concentrating microorganisms from fluid comprising the steps of:
   a. continuously feeding the fluid into a flow path, the flow path including a separation section oriented within planes generally perpendicular to the axis of rotation, and wherein the separation section has a length greater than 2 r, where r is the average of the maximum and minimum radial distances of the flow path from the rotational axis; and
   b. subjecting the flow path to centrifugal forces by spinning the flow path about the rotational axis.

35. The method of claim 34 wherein the separation section has a length greater than 2 πr.

36. The method of claim 34 wherein after spinning the flow path, at least a portion of the fluid therein is tested for the presence of pathogenic organisms.

37. The method of claim 34 wherein the surfaces defining the flow path are at least partially coated with a surfactant.

38. The method of claim 34 wherein the flow path includes a fluid input line and a fluid exit line, each situated near an end of the flow path.

39. The method of claim 38 wherein the input and exit lines are adjacent each other on the flow path with a barrier resting therebetween.

40. The method of claim 38 wherein at least one of the input and exit lines is substantially radially oriented toward the rotational axis.

41. The method of claim 34 wherein the separation section includes the point on the flow path which is spaced at the maximum radial extent from the rotational axis.

42. The method of claim 34 wherein the flow path is defined by a channel centrifuge.

43. The method of claim 34 wherein the fluid is filtered after centrifugation.

* * * * *